United States Patent
Chian

(10) Patent No.: US 12,288,330 B2
(45) Date of Patent: Apr. 29, 2025

(54) MEDICAL AUXILIARY INFORMATION GENERATION METHOD AND MEDICAL AUXILIARY INFORMATION GENERATION SYSTEM

(71) Applicant: Wistron Corporation, New Taipei (TW)

(72) Inventor: Guan Yi Chian, New Taipei (TW)

(73) Assignee: Wistron Corporation, New Taipei (TW)

( * ) Notice: Subject to any disclaimer, the term of this patent is extended or adjusted under 35 U.S.C. 154(b) by 396 days.

(21) Appl. No.: 17/827,769

(22) Filed: May 29, 2022

(65) Prior Publication Data
US 2023/0316503 A1    Oct. 5, 2023

(30) Foreign Application Priority Data
Mar. 30, 2022    (TW) .................. 111112157

(51) Int. Cl.
G06T 7/00        (2017.01)
G06T 7/11        (2017.01)
G16H 30/40       (2018.01)

(52) U.S. Cl.
CPC ............. G06T 7/0012 (2013.01); G06T 7/11 (2017.01); G16H 30/40 (2018.01);
(Continued)

(58) Field of Classification Search
CPC ............ G06T 7/0012; G06T 7/11; G06T 2207/20081; G06T 2207/20084; G06T 2207/30021; G16H 30/40
See application file for complete search history.

(56) References Cited

U.S. PATENT DOCUMENTS

2013/0329973 A1* 12/2013 Cao ................. G06T 7/0016
                                                382/128
2015/0044098 A1*  2/2015 Smart ................ A61B 5/0064
                                                422/82.05
(Continued)

FOREIGN PATENT DOCUMENTS

CN    105550651    5/2016
CN    107240102    10/2017
(Continued)

OTHER PUBLICATIONS

"Office Action of Taiwan Counterpart Application", issued on Jun. 29, 2023, p. 1-p. 11.
(Continued)

Primary Examiner — John J Lee
(74) Attorney, Agent, or Firm — JCIPRNET

(57) ABSTRACT

A medical auxiliary information generation method and a medical auxiliary information generation system are provided. The method includes: obtaining a physiological image; identifying a target image region from the physiological image through at least one artificial intelligence model, wherein each pixel position in the target image region corresponds to an estimation value, and the estimation value meets a default condition; determining at least one target pixel position in the target image region according to a numerical distribution of the estimation value; and generating medical auxiliary information according to the target pixel position, wherein the medical auxiliary information carries prompt information related to the target pixel position.

20 Claims, 7 Drawing Sheets

(52) U.S. Cl.
CPC .............. *G06T 2207/20081* (2013.01); *G06T 2207/20084* (2013.01); *G06T 2207/30021* (2013.01)

(56) References Cited

U.S. PATENT DOCUMENTS

2020/0193236 A1* 6/2020 Oosake ................ G06V 10/454
2022/0036542 A1* 2/2022 Sainz de Cea ....... G06T 7/0012

FOREIGN PATENT DOCUMENTS

| | | |
|---|---|---|
| CN | 107368670 | 11/2017 |
| CN | 109671053 | 4/2019 |

OTHER PUBLICATIONS

Wen Pan et al., "Identification of Barrett's esophagus in endoscopic images using deep learning", BioMed Central gastroenterology, Dec. 2021, pp. 1-8.

Albert J De Groof et al., "Deep-Learning System Detects Neoplasia in Patients With Barrett's Esophagus With Higher Accuracy Than Endoscopists in a Multistep Training and Validation Study With Benchmarking", American Gastroenterological Association, Gastroenterology, Nov. 2019, pp. 1-19.

"Search Report of Europe Counterpart Application", issued on Jan. 16, 2023, p. 1-p. 12.

* cited by examiner

MEDICAL AUXILIARY INFORMATION GENERATION METHOD AND MEDICAL AUXILIARY INFORMATION GENERATION SYSTEM

CROSS-REFERENCE TO RELATED APPLICATION

This application claims the priority benefit of Taiwan application serial no. 111112157, filed on Mar. 30, 2022. The entirety of the above-mentioned patent application is hereby incorporated by reference herein and made a part of this specification.

BACKGROUND

Technical Field

The disclosure relates to an image analysis technology, and more particularly to a medical auxiliary information generation method and a medical auxiliary information generation system.

Description of Related Art

Esophageal cancer is one of the most common types of cancer, and there is a 50% probability of esophageal cancer developing from Barrett's esophagus. Generally speaking, during the examination, the doctor captures an image of the gastroesophageal (EG) junction of a patient through gastroscopy, and manually and preliminarily judges whether the patient has Barrett's esophagus according to the obtained image. If the patient is judged to have a high probability of having Barrett's esophagus, the doctor will perform biopsy on the region suspected to be Barrett's esophagus and execute pathological analysis according to the result of the biopsy, thereby determining whether the patient does have Barrett's esophagus. However, the above detection manner (including the preliminary diagnosis of Barrett's esophagus and the selection of subsequent biopsy position) are highly dependent on the experience and the physical and mental state of the doctor.

SUMMARY

The disclosure provides a medical auxiliary information generation method and a medical auxiliary information generation system, which can improve the detection efficiency for a specific symptom of the human body.

An embodiment of the disclosure provides a medical auxiliary information generation method, which includes the following steps. A physiological image is obtained. A target image region is identified from the physiological image through at least one artificial intelligence model. Each pixel position in the target image region corresponds to an estimation value, and the estimation value meets a default condition. At least one target pixel position is determined in the target image region according to a numerical distribution of the estimation value. Medical auxiliary information is generated according to the at least one target pixel position. The medical auxiliary information carries prompt information related to the at least one target pixel position.

An embodiment of the disclosure further provides a medical auxiliary information generation system, which includes a storage circuit and a processor. The storage circuit is configured to store a physiological image. The processor is coupled to the storage circuit. The processor is configured to perform the following. The physiological image is obtained. A target image region is identified from the physiological image through at least one artificial intelligence model. Each pixel position in the target image region corresponds to an estimation value, and the estimation value meets a default condition. At least one target pixel position is determined in the target image region according to a numerical distribution of the estimation value. Medical auxiliary information is generated according to the at least one target pixel position. The medical auxiliary information carries prompt information related to the at least one target pixel position.

Based on the above, after obtaining the physiological image, the at least one artificial intelligence model may be configured to identify the target image region from the physiological image. In particular, each pixel position in the target image region corresponds to an estimation value, and the estimation value needs to meet the default condition. Then, the at least one target pixel position in the target image region may be determined according to the numerical distribution of the estimation value, and the medical auxiliary information may be generated according to the target pixel position. In particular, the medical auxiliary information may carry the prompt information related to the target pixel position. Thereby, the detection efficiency for the specific symptom of the human body can be improved.

DETAILED DESCRIPTION OF DISCLOSED EMBODIMENTS

Figure 1:
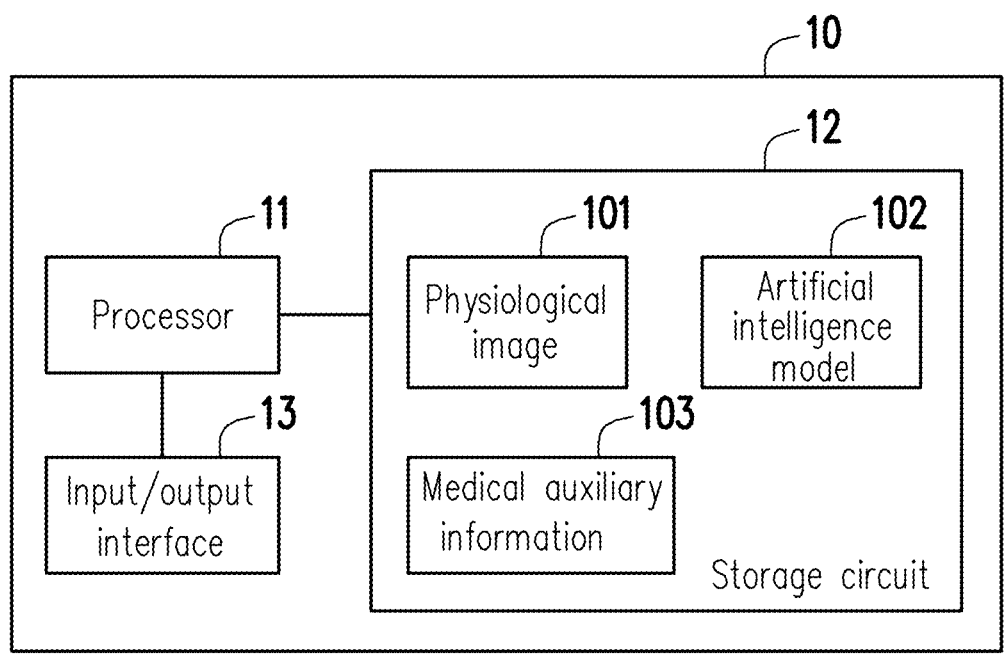
FIG. 1 is a schematic diagram of a medical auxiliary information generation system according to an embodiment of the disclosure.

FIG. 1 is a schematic diagram of a medical auxiliary information generation system according to an embodiment of the disclosure. Please refer to FIG. 1. A medical auxiliary information generation system 10 may be disposed in various electronic devices supporting image processing technology, such as a smart phone, a notebook computer, a desktop computer, a tablet computer, an industrial computer, or a server.

The medical auxiliary information generation system 10 may include a processor 11, a storage circuit 12, and an input/output (I/O) interface 13. The processor 11 is configured to be responsible for the overall or partial operation of the medical auxiliary information generation system 10. For example, the processor 11 may include a central processing unit (CPU), a graphic processing unit (GPU), other programmable general-purpose or specific-purpose microprocessors, digital signal processors (DSPs), programmable controllers, application specific integrated circuits (ASICs), programmable logic devices (PLDs), other similar devices, or a combination of the devices.

The storage circuit 12 is coupled to the processor 11 and is configured to store data. For example, the storage circuit 12 may include a volatile storage circuit and a non-volatile storage circuit. The volatile storage circuit is configured for volatile storage of data. For example, the volatile storage circuit may include a random access memory (RAM) or similar volatile storage media. The non-volatile storage circuit is configured for non-volatile storage of data. For example, the non-volatile storage circuit may include a read only memory (ROM), a solid state disk (SSD), a hard disk drive (HDD), or similar non-volatile storage media.

The input/output interface 13 is coupled to the processor 11 and is configured to execute signal input and output. For example, the input/output interface 13 may include various input/output devices, such as a camera, a display, a network interface card, a mouse, a keyboard, a touch pad, a speaker, and a microphone. The disclosure does not limit the type of the input/output device.

The processor 11 may obtain a physiological image 101 and store the physiological image 101 in the storage circuit 12. The physiological image 101 may reflect a health state or a disease symptom of the body of a patient. In the following embodiments, the detection of whether there is Barrett's esophagus in the esophagus of the patient is taken as an example, so the physiological image 101 may include an esophagus image of the patient, but the disclosure is not limited thereto. For example, if there is Barrett's esophagus in the esophagus of the patient, there may be image features of Barrett's esophagus in the physiological image 101. Alternatively, if there are other types of disease symptoms in the esophagus of the patient, there may also be corresponding image features in the physiological image 101. In addition, the physiological image 101 may also reflect health states or disease symptoms of other parts of the human body, which is not limited in the disclosure.

The processor 11 may identify a specific image region (also referred to as a target image region) from the physiological image 101 through the artificial intelligence model 102. For example, the target image region may include an image region covered by the image features of Barrett's esophagus. In particular, each pixel position in the target image region may correspond to an estimation value, and the estimation value needs to meet a specific condition (also referred to as a default condition). For example, the default condition may define that the estimation value corresponding to each pixel position in the target image region must be greater than a specific value (also referred to as a default value). For example, the default value may be 0.5 or other values between 0 and 1.

In an embodiment, the artificial intelligence model 102 is implemented as a software module and is stored in the storage circuit 12. Alternatively, in an embodiment, the artificial intelligence model 102 may also be implemented in a hardware circuit (for example, an image processing chip). The artificial intelligence model 102 may have an artificial intelligence architecture, such as machine learning and/or deep learning. For example, the artificial intelligence model 102 may adopt a neural network model involving encoding and decoding, such as a convolutional neural network (CNN) model, a full convolutional network (FCN) model, a region-based CNN, and/or a U-Net model. The processor 11 may run the artificial intelligence model 102 to execute automated image identification on the physiological image 101. In addition, the artificial intelligence model 102 may continuously improve the image identification performance (for example, the accuracy of image identification) thereof through training.

In an embodiment, the processor 11 may input the physiological image 101 to the artificial intelligence model 102. The artificial intelligence model 102 may analyze the physiological image 101 and output an estimation value for each (or at least part of) pixel position in the physiological image 101. In particular, the estimation value corresponding to a certain pixel position may reflect the probability of the artificial intelligence model 102 identifying that the pixel position belongs to Barrett's esophagus. The processor 11 may determine the estimation value corresponding to each pixel position in the physiological image 101 according to the output of the artificial intelligence model 102.

In an embodiment, the processor 11 may judge whether the estimation value corresponding to a specific pixel position (also referred to as a first pixel position) in the physiological image 101 is greater than the default value. In response to the estimation value corresponding to the first pixel position being greater than the default value, the processor 11 may judge that the estimation value corresponding to the first pixel position meets the default condition and incorporate the first pixel position into the target image region. Alternatively, in response to the estimation value corresponding to the first pixel position being not greater than the default value, the processor 11 may judge that the estimation value corresponding to the first pixel position does not meet the default condition and not incorporate the first pixel position into the target image region. Through preliminarily selecting the target image region, the processor 11 may preliminarily determine which image regions in the physiological image 101 have the image features of Barrett's esophagus.

After obtaining the target image region, the processor 11 may determine at least one specific pixel position (also referred to as a target pixel position) in the target image region according to numerical distributions of the estimation values corresponding to multiple pixel positions in the target image region. The target pixel position may include a position in the target image region with a relatively high probability of Barrett's esophagus as identified by the artificial intelligence model 102.

In an embodiment, the processor 11 may compare the estimation values corresponding to multiple pixel positions (also referred to as candidate pixel positions) in the target image region. Then, the processor 11 may determine the target pixel position from the candidate pixel positions according to a comparison result. For example, a candidate pixel position corresponding to the maximum estimation value among the candidate pixel positions indicates that the artificial intelligence model 102 has a relatively high probability of identifying Barrett's esophagus at the candidate pixel position. Therefore, the processor 11 may determine the candidate pixel position corresponding to the maximum estimation value among the candidate pixel positions as the target pixel position.

In an embodiment, the total number of target pixel positions may be one. In an embodiment, the total number of target pixel positions may be multiple. In the case where the total number of target pixel positions is multiple, the distance between any two target pixel positions may be limited to be greater than a default distance value. For example, assuming that the target pixel positions include a first target pixel position and a second target pixel position, the distance between the first target pixel position and the second target pixel position needs to be greater than the default distance value. If the distance between a certain candidate pixel position and a specific target pixel position is not greater than the default distance value, the candidate pixel position will not be allowed to be used as the target pixel position or be excluded from the target pixel positions.

After determining the target pixel position, the processor 11 may generate medical auxiliary information 103 according to the target pixel position. For example, the medical auxiliary information 103 may be stored in the storage circuit 12. In particular, the medical auxiliary information 103 may carry prompt information related to the target pixel position. For example, the prompt information may include coordinate information of the target pixel position and/or present the target pixel position in the target image region (or the physiological image 101) through a specific visual effect. In an embodiment, the medical auxiliary information 103 may also carry prompt information related to the target image region. For example, the prompt information may include coordinate information of the target image region and/or present the target image region in the physiological image 101 through a specific visual effect.

In an embodiment, the doctor may determine the actual position in the esophagus of the patient to perform biopsy to detect Barrett's esophagus according to the prompt information related to the target pixel position (or the target image region) in the medical auxiliary information 103. In an embodiment, through performing biopsy on a part of the esophagus corresponding to the target pixel position, the accuracy of detecting Barrett's esophagus can be effectively improved.

Figure 2:
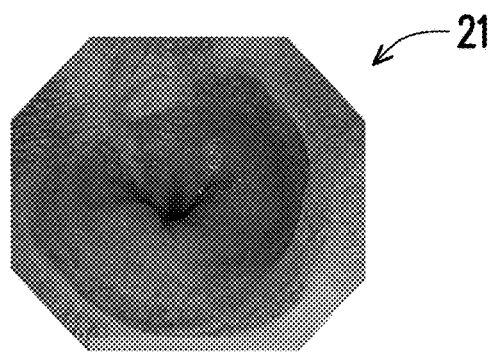
FIG. 2 is a schematic diagram of a physiological image according to an embodiment of the disclosure.
Figure 3:
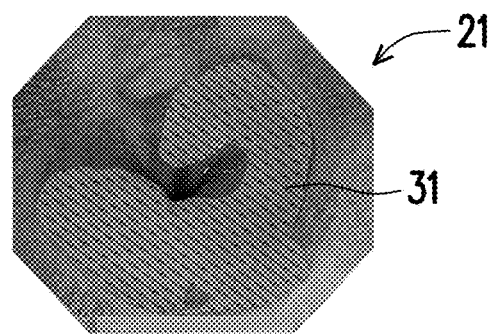
FIG. 3 is a schematic diagram of a target image region according to an embodiment of the disclosure.
Figure 4:
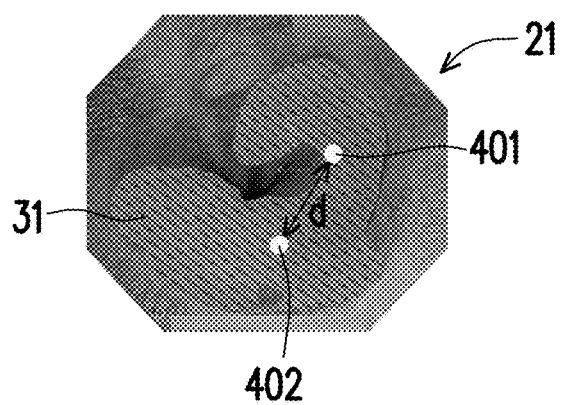
FIG. 4 is a schematic diagram of a target pixel position according to an embodiment of the disclosure.

FIG. 2 is a schematic diagram of a physiological image according to an embodiment of the disclosure. FIG. 3 is a schematic diagram of a target image region according to an embodiment of the disclosure. FIG. 4 is a schematic diagram of a target pixel position according to an embodiment of the disclosure.

Please refer to FIG. 1 to FIG. 4. It is assumed that the physiological image 101 includes an image 21. The processor 11 may identify an image region 31 (that is, the target image region, the region marked with diagonal lines in FIG. 3) from the image 21 through the artificial intelligence model 102. For example, the image region 31 may include an image region covered by Barrett's esophagus as identified by the artificial intelligence model 102. Then, the processor 11 may determine pixel positions 401 and/or 402 in the image region 31 as the target pixel positions according to numerical distributions of estimation values corresponding to at least part of the pixel positions (that is, candidate pixel positions) in the image region 31. For example, the estimation value corresponding to the pixel position 401 may be greater than the estimation value corresponding to at least one pixel position near or around the pixel position 401, and the estimation value corresponding to the pixel position 402 may be greater than the estimation value corresponding to at least one pixel position near or around the pixel position 402. In other words, the pixel positions 401 and 402 may include positions in the image region 31 with relatively high probabilities of Barrett's esophagus as identified by the artificial intelligence model 102. Then, the processor 11 may generate the medical auxiliary information 103 according to the pixel positions 401 and/or 402. The medical auxiliary information 103 may carry prompt information related to the pixel positions 401 and/or 402 (for example, coordinate information of the pixel positions 401 and/or 402). Thereafter, the medical auxiliary information 103 may be configured to recommend the pixel positions 401 and/or 402 as suitable positions for biopsy in the esophagus of the patient to the doctor, so as to improve the accuracy of subsequent diagnosis of Barrett's esophagus.

In an embodiment, the processor 11 may determine a pixel position corresponding to the maximum estimation value in the image region 31 as the target pixel position. In another embodiment, if multiple pixel positions corresponding to relatively large estimation values are concentrated in a specific block, the processor 11 may select a pixel position at the center of the specific block as the target pixel position.

It should be noted that in the case where the pixel positions 401 and 402 are used as the target pixel positions at the same time, in the image 21, a distance (also referred to as a pixel distance) d between the pixel positions 401 and 402 needs to be greater than a default distance value. For example, a distance corresponding to the default distance value in a physical space (also referred to as an actual distance) may be 10 millimeters (mm) or other values. Thereby, the accuracy of subsequent biopsy can be effectively improved. In addition, in an embodiment, more pixel positions in the image region 31 may also be determined as the target pixel positions to be used as reference positions for biopsy, which is not limited in the disclosure.

In an embodiment, the processor 11 may convert the distance d in the image 21 into the actual distance in the physical space or convert the actual distance in the physical space into the distance d in the image 21 according to a conversion equation. In an embodiment, the processor 11 obtains distance information (for example, the distance d) between pixels from the physiological image 101 in DICOM format, thereby calculating the actual distance between the pixel positions 401 and 402 according to the distance information.

In an embodiment, after selecting the pixel position 401 as the target pixel position, the processor 11 may select the qualified pixel position 402 as the target pixel position according to the default distance value. Alternatively, in an embodiment, the processor 11 may also first select the pixel position 402 as the target pixel position, and then select the pixel position 401 as the target pixel position according to the default distance value, as long as the selected pixel positions 401 and 402 meet the default condition (that is, the distance d between the pixel positions 401 and 402 is greater than the default distance value).

In an embodiment, it is assumed that the pixel position 401 is first determined as the target pixel position. In the case where the distance d between the pixel positions 401 and 402 is not greater than the default distance value, even if the estimation value corresponding to the pixel position 402 is very large, the processor 11 may still ignore the pixel position 402 and not determine the pixel position 402 as the target pixel position.

In an embodiment, the total number of artificial intelligence models 102 may be one. In the case where the total number of artificial intelligence models 102 is one, the artificial intelligence model 102 may be configured to analyze the physiological image 101 and output the estimation value for each pixel position in the physiological image 101 to reflect the probability of each pixel position in the physiological image 101 belonging to Barrett's esophagus. The processor 11 may directly use the estimation value output by the artificial intelligence model 102 to determine the target image region and the target pixel position in the physiological image 101. The relevant operation details have been described in detail above and will not be repeated.

In an embodiment, the total number of artificial intelligence models 102 may also be multiple. In the case where the total number of artificial intelligence models 102 is multiple, the artificial intelligence models 102 may include at least a first artificial intelligence model and a second artificial intelligence model. The first artificial intelligence model and the second artificial intelligence model may both be configured to analyze the physiological image 101 and output the estimation value for each pixel position in the physiological image 101 to reflect the probability of each pixel position in the physiological image 101 belonging to Barrett's esophagus. The processor 11 may obtain the estimation value (also referred to as a first estimation value) corresponding to each pixel position in the physiological image 101 according to the output of the first artificial intelligence model. On the other hand, the processor 11 may obtain the estimation value (also referred to as a second estimation value) corresponding to each pixel position in the physiological image 101 according to the output of the second artificial intelligence model. Next, the processor 11 may determine the estimation value (also referred to as a third estimation value) corresponding to each pixel position in the physiological image 101 according to the first estimation value and the second estimation value. Afterwards, the processor 11 may determine the target image region and the target pixel position according to the estimation value (that is, the third estimation value) corresponding to each pixel position in the physiological image 101. The relevant operation details have been described in detail above and will not be repeated.

Figure 5:
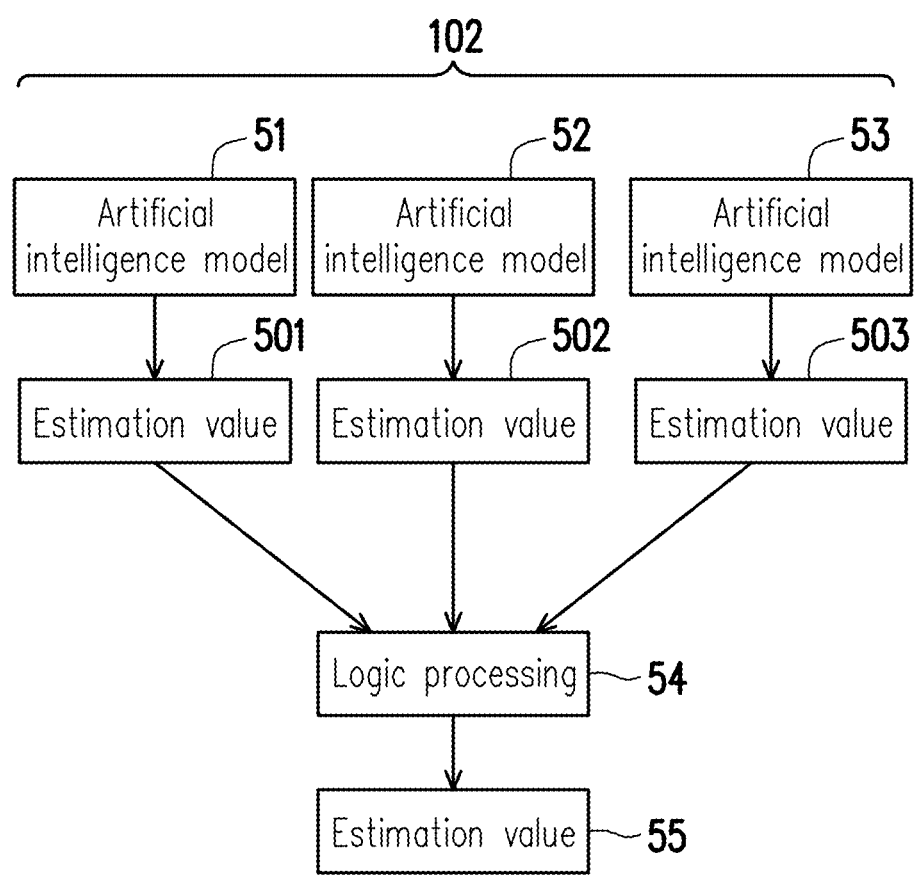
FIG. 5 is a schematic diagram of obtaining estimation values according to outputs of multiple artificial intelligence models according to an embodiment of the disclosure.

FIG. 5 is a schematic diagram of obtaining estimation values according to outputs of multiple artificial intelligence models according to an embodiment of the disclosure. Please refer to FIG. 1 and FIG. 5. It is assumed that the artificial intelligence model 102 includes artificial intelligence models 51 to 53. The artificial intelligence models 51 to 53 may analyze the physiological image 101 of FIG. 1 and respectively output estimation values 501 to 503. In particular, the estimation value 501 may reflect the probability of a certain pixel position in the physiological image 101 belonging to Barrett's esophagus judged by the artificial intelligence model 51, the estimation value 502 may reflect the probability of a certain pixel position in the physiological image 101 belonging to Barrett's esophagus as judged by the artificial intelligence model 52, and the estimation value 503 may reflect the probability of a certain pixel position in the physiological image 101 belonging to Barrett's esophagus as judged by the artificial intelligence model 53.

The processor 11 may execute logic processing 54 according to the estimation values 501 to 503 to generate an estimation value 55. For example, the logic processing 54 may include various logic computations such as performing numerical averaging on the estimation values 501 to 503. The estimation value 55 may reflect an operation result of executing the logic processing 54 on the estimation values 501 to 503. For example, assuming that the estimation value 55 is the average value of the estimation values 501 to 503, the estimation value 55 may reflect the average probability of a certain pixel position in the physiological image 101 belonging to Barrett's esophagus as judged by the artificial intelligence models 51 to 53. Thereafter, the processor 11 may determine the target image region and the target pixel position according to the estimation value 55. The relevant operation details have been described in detail above and will not be repeated.

Figure 6:
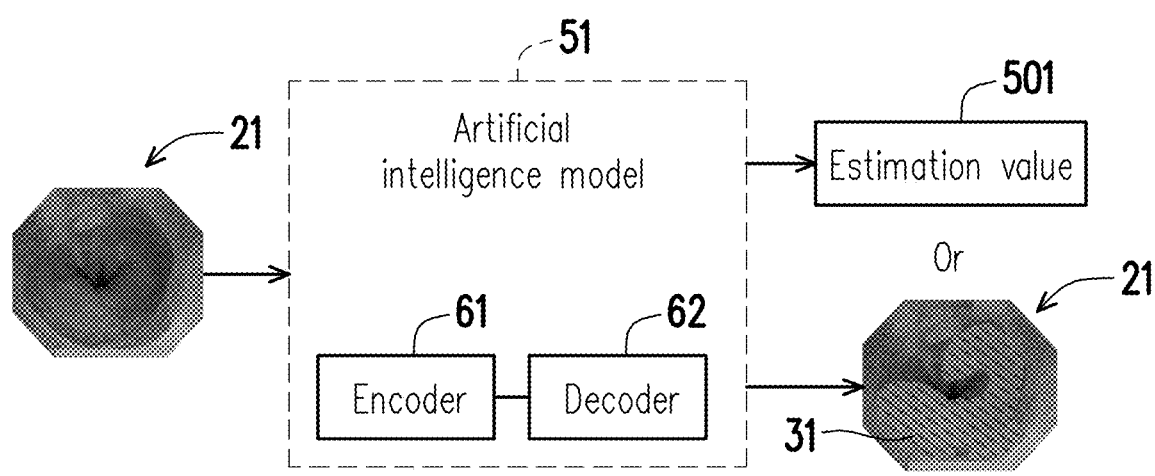
FIG. 6 is a schematic diagram of analyzing a physiological image by an artificial intelligence model according to an embodiment of the disclosure.

FIG. 6 is a schematic diagram of analyzing a physiological image by an artificial intelligence model according to an embodiment of the disclosure. Please refer to FIG. 5 and FIG. 6. Taking the artificial intelligence model 51 as an example, the artificial intelligence model 51 may include an encoder 61 and a decoder 62. The encoder 61 is coupled to the input of the artificial intelligence model 51. The decoder 62 is coupled to the output of the encoder 61 and the output of the artificial intelligence model 51. For example, the encoder 61 may adopt EfficientNetB3 as the backbone network to learn image features, and use ImageNet to pretrain network weights for transfer learning. The decoder 62 may adopt U-Net as the backbone network to output the estimation value corresponding to each pixel position in the image.

It should be noted that in the decoder 62, an up-sampling layer for expanding a decoded pixel area may be replaced with a deconvolution layer to optimize the learning ability of the artificial intelligence model 51. In addition, the decoder 62 may adopt a sigmoid function as an activation function to output the estimation value corresponding to each pixel position in the image.

Taking the analysis of the image 21 in FIG. 2 as an example, after the image 21 is input to the artificial intelligence model 51, the encoder 61 may first encode the image 21 through an EfficientNetB3 network. Then, the decoder 62 may decode an operation result of the encoder 61 through a customized U-Net network (including the deconvolution layer) and generate the estimation value 501. Alternatively, in an embodiment, the artificial intelligence model 51 may directly output the identified image region 31 in the image 21 according to the estimation value 501. Alternatively, in an embodiment, a first part of the artificial intelligence model 51 may be configured to analyze the image 21 and output the image region 31, and a second part of the artificial intelligence model 51 may be configured to determine the target pixel position from the image region 31.

In an embodiment, in the case where the total number of artificial intelligence models 102 is multiple, the processor 11 may use specific training data (also referred to as first training data) to train the first artificial intelligence model among the artificial intelligence models 102 and use specific verification data (also referred to as first verification data) to verify the trained first artificial intelligence model. On the other hand, the processor 11 may use another training data (also referred to as second training data) to train the second artificial intelligence model among the artificial intelligence models 102. In addition, the processor 11 may use another verification data (also referred to as second verification data) to verify the trained second artificial intelligence model. In particular, the second training data is different from the first training data, and the second training data for training the second artificial intelligence model may include the first verification data for verifying the first artificial intelligence model. In addition, the second verification data may include at least part of the first training data. Through cross-using the training data and the verification data for different artificial intelligence models, the training efficiency for multiple artificial intelligence models can be effectively improved.

Figure 7:
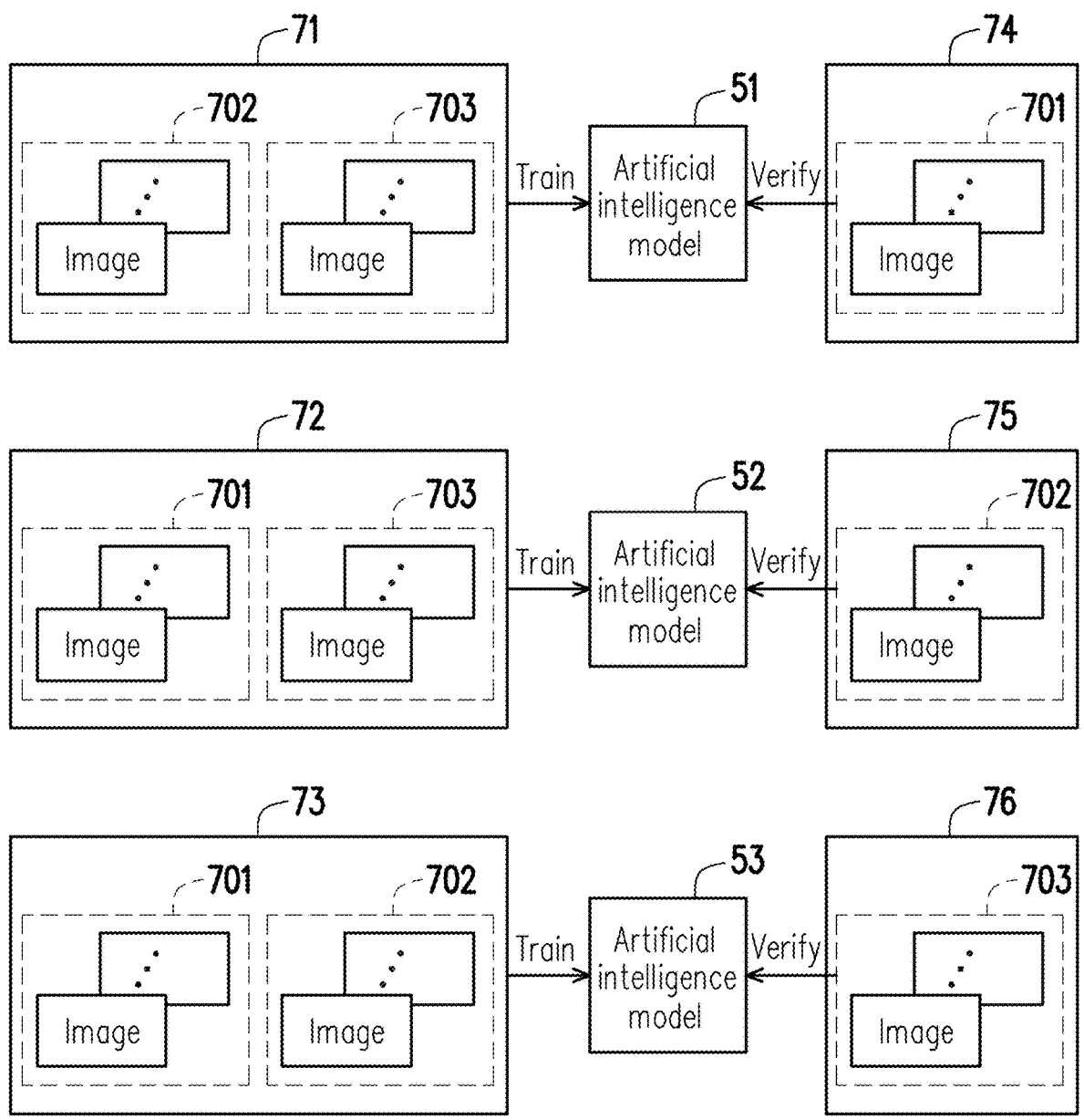
FIG. 7 is a schematic diagram of training multiple artificial intelligence models according to an embodiment of the disclosure.

FIG. 7 is a schematic diagram of training multiple artificial intelligence models according to an embodiment of the disclosure. Please refer to FIG. 7. Taking the training of the artificial intelligence models 51 to 53 in FIG. 5 as an example, training data 71 to 73 may be respectively configured to train the artificial intelligence models 51 to 53, and verification data 74 to 76 may be respectively configured to verify the trained artificial intelligence models 51 to 53. For example, after respectively using the training data 71 to 73 to train the artificial intelligence models 51 to 53, the verification data 74 to 76 may be respectively configured to verify the image identification ability of the trained artificial intelligence models 51 to 53. In addition, according to verification results, decision making parameters in the artificial intelligence models 51 to 53 may also be adjusted accordingly to optimize the decision making ability.

It should be noted that the training data 71 may include image data 702 and 703, the training data 72 may include image data 701 and 703, and the training data 73 may include the image data 701 and 702. In addition, the verification data 74 may include the image data 701, the verification data 75 may include the image data 702, and the verification data 76 may include the image data 703. The image data 701 to 703 may respectively include esophagus images of one or more patients, and the esophagus images may or may not include the image features of Barrett's esophagus. In addition, at least part of the images in the image data 701 to 703 may be subjected to image processing means such as scaling, rotation, and/or color adjustment, so as to improve the diversity of the training data.

From another perspective, the common training data 701 for the artificial intelligence models 52 and 53 may be used to verify the image identification ability of the artificial intelligence model 51, the common training data 702 for the artificial intelligence models 51 and 53 may be used to verify the image identification ability of the artificial intelligence model 52, and the common training data 703 for the artificial intelligence models 51 and 52 may be used to verify the image identification ability of the artificial intelligence model 53. In an embodiment, through cross-using the training data for other artificial intelligence models as the verification data of a specific artificial intelligence model, the training and verification efficiency of the artificial intelligence model can be effectively improved.

It should be noted that although the embodiments of FIG. 5 and FIG. 7 both use 3 artificial intelligence models as examples of the artificial intelligence model 102, the disclosure is not limited thereto. In other embodiments, the artificial intelligence model 102 may also include more (for example, 5) or less (for example, 2) artificial intelligence models, and the usage and training manners of the models have been described in detail above and will not be repeated.

Figure 8:
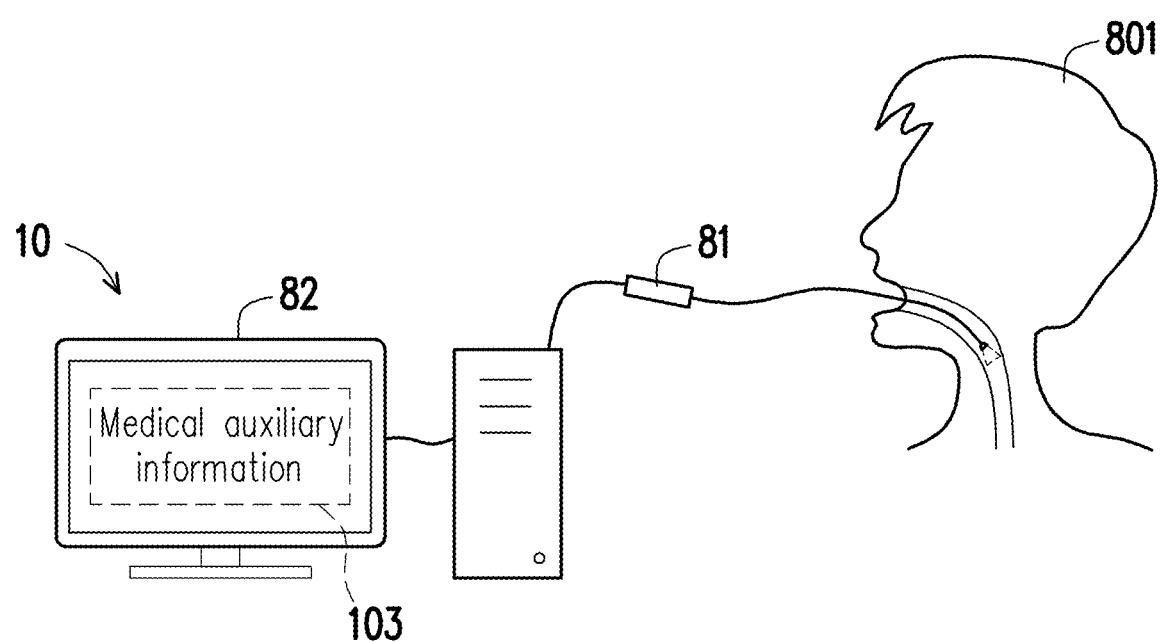
FIG. 8 is a schematic diagram of a medical auxiliary information generation system according to an embodiment of the disclosure.

FIG. 8 is a schematic diagram of a medical auxiliary information generation system according to an embodiment of the disclosure. Please refer to FIG. 1 and FIG. 8. In an embodiment, the input/output interface 13 may include a camera 81 and/or a display 82.

The camera 81 may include a miniature camera (or a miniature camera lens). The lens of the camera 81 may be inserted deep into the esophagus of a patient 801 to perform esophagus photography, so as to capture an internal image of the esophagus of the patient 801, as shown in FIG. 8. Therefore, the physiological image 101 may include an image captured through the camera 81 deep into the esophagus of the patient 801. In addition, the display 82 may be configured to present the medical auxiliary information 103 for the doctor to view.

In an embodiment, the display 82 may display the target image region or the target pixel position as shown in FIG. 3 or FIG. 4. In an embodiment, the processor 11 of FIG. 1 may overlay a layer marked with the target image region on the physiological image 101 and/or add a bright spot marked with the target pixel position on the physiological image 101. After overlaying the layer marked with the target image region on the physiological image 101 and/or adding the bright spot marked with the target pixel position on the physiological image 101, the processor 11 may display the processed image on the display 82, thereby presenting the medical auxiliary Information 103.

In an embodiment, the medical auxiliary information generation system 10 may include a model for identifying an image of a gastroesophageal junction, and the model may be stored in the storage circuit 12 of FIG. 1. When the camera 81 performs the esophagus photography, the processor 11 may input multiple internal images of the esophagus of the patient 801 obtained through the camera 81 to the model for identifying the image of the gastroesophageal junction, and the model may be configured to find the image of the gastroesophageal junction from the internal images of the esophagus. For example, the image of the gastroesophageal junction may include the physiological image 101 of FIG. 1 (or the image 21 of FIG. 2).

Figure 9:
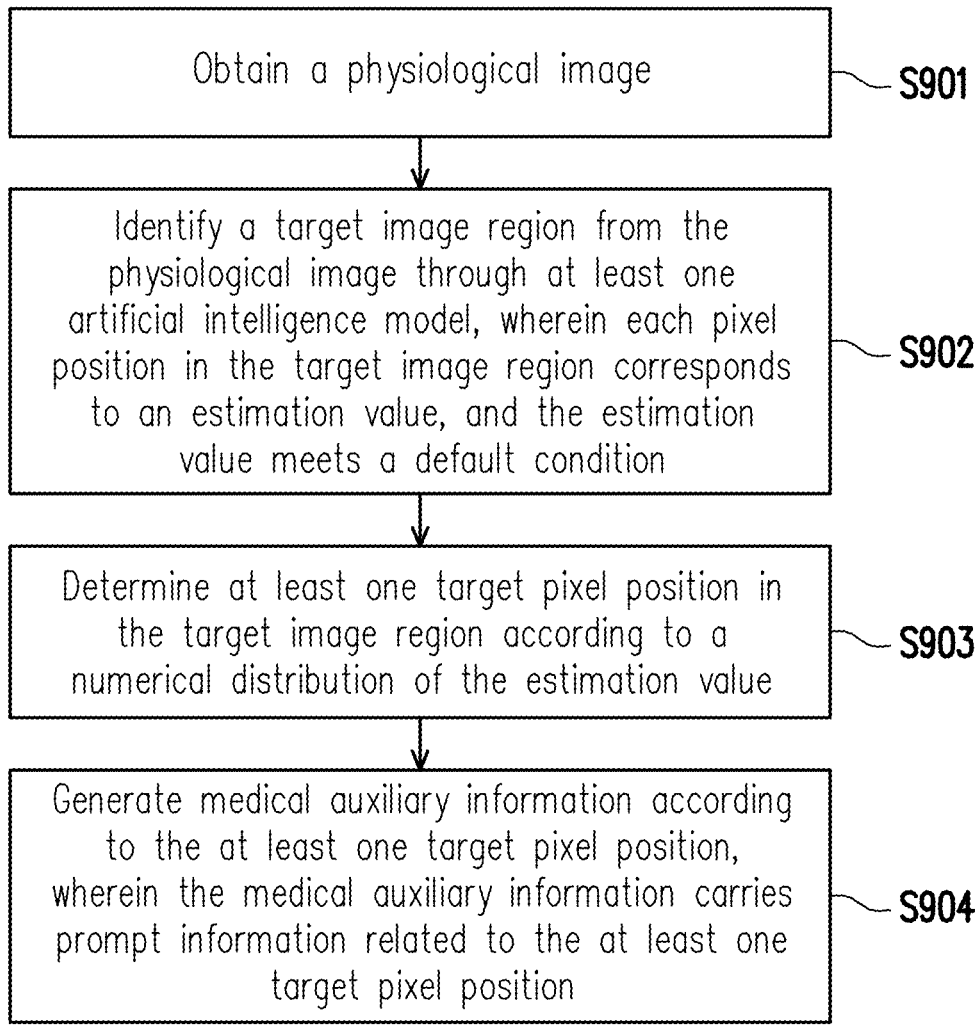
FIG. 9 is a flowchart of a medical auxiliary information generation method according to an embodiment of the disclosure.

FIG. 9 is a flowchart of a medical auxiliary information generation method according to an embodiment of the disclosure. Please refer to FIG. 9. In Step S901, a physiological image is obtained. For example, the physiological image may reflect the esophagus state of a patient. In Step S902, a target image region is identified from the physiological image through at least one artificial intelligence model, wherein each pixel position in the target image region corresponds to an estimation value, and the estimation value meets a default condition. In Step S903, at least one target pixel position is determined in the target image region according to a numerical distribution of the estimation value. In Step S904, medical auxiliary information is generated according to the at least one target pixel position, wherein the medical auxiliary information carries prompt information related to the at least one target pixel position.

However, each step in FIG. 9 has been described in detail as above and will not be repeated. It is worth noting that each step in FIG. 9 may be implemented as multiple program codes or circuits, which is not limited in the disclosure. In addition, the method of FIG. 9 may be used in conjunction with the above exemplary embodiments or may be used alone, which is not limited in the disclosure.

In summary, the two-stage image detection and pixel position screening technology (the first stage is to identify the target image region, and the second stage is to determine the target pixel position) is executed by the artificial intelligence model, and the determined target pixel position may be recommended to the user (for example, the doctor) as the reference position for executing biopsy, thereby improving the detection accuracy of diseases, such as Barrett's esophagus. In addition, through adopting the customized artificial intelligence model and the cross-training and verification mechanism for multiple models, the image identification ability of the artificial intelligence model can also be effectively improved.

Although the disclosure has been disclosed in the above embodiments, the embodiments are not intended to limit the disclosure. Persons skilled in the art may make some changes and modifications without departing from the spirit and scope of the disclosure. Therefore, the protection scope of the disclosure shall be defined by the appended claims.

What is claimed is:

1. A medical auxiliary information generation method, comprising:
obtaining a physiological image;

identifying a target image region from the physiological image through at least one artificial intelligence model, wherein each pixel position in the target image region corresponds to an estimation value, and the estimation value meets a default condition;

determining at least one target pixel position in the target image region according to a numerical distribution of the estimation value; and generating medical auxiliary information according to the at least one target pixel position, wherein the medical auxiliary information carries prompt information related to the at least one target pixel position.

2. The medical auxiliary information generation method according to claim 1, wherein the step of identifying the target image region from the physiological image through the at least one artificial intelligence model comprises:

inputting the physiological image to the at least one artificial intelligence model;

determining the estimation value corresponding to each pixel position in the physiological image according to an output of the at least one artificial intelligence model; and according to the estimation value corresponding to the each pixel position in the physiological image, determining the target image region in the physiological image.

3. The medical auxiliary information generation method according to claim 2, wherein the at least one artificial intelligence model comprises a first artificial intelligence model and a second artificial intelligence model, and the step of determining the estimation value corresponding to the each pixel position in the physiological image according to the output of the at least one artificial intelligence model comprises:

according to an output of the first artificial intelligence model, obtaining a first estimation value corresponding to the each pixel position in the physiological image;

according to an output of the second artificial intelligence model, obtaining a second estimation value corresponding to the each pixel position in the physiological image; and determining a third estimation value corresponding to the each pixel position in the physiological image according to the first estimation value and the second estimation value.

4. The medical auxiliary information generation method according to claim 2, wherein the step of according to the estimation value corresponding to the each pixel position in the physiological image, determining the target image region in the physiological image comprises:

judging whether an estimation value corresponding to a first pixel position in the physiological image is greater than a default value; and in response to the estimation value corresponding to the first pixel position being greater than the default value, incorporating the first pixel position into the target image region.

5. The medical auxiliary information generation method according to claim 4, wherein the step of determining the at least one target pixel position in the target image region according to the numerical distribution of the estimation value comprises:

comparing estimation values corresponding to a plurality of candidate pixel positions in the target image region; and determining the at least one target pixel position from the candidate pixel positions according to a comparison result.

6. The medical auxiliary information generation method according to claim 5, wherein the step of determining the at least one target pixel position from the candidate pixel positions according to the comparison result comprises:

determining a candidate pixel position corresponding to a maximum estimation value among the candidate pixel positions as one of the at least one target pixel position.

7. The medical auxiliary information generation method according to claim 1, wherein the at least one target pixel position comprises a first target pixel position and a second target pixel position, and a distance between the first target pixel position and the second target pixel position is greater than a default distance value.

8. The medical auxiliary information generation method according to claim 1, wherein the at least one artificial intelligence model comprises a first artificial intelligence model and a second artificial intelligence model, and the medical auxiliary information generation method further comprises:

training the first artificial intelligence model using first training data;

verifying the trained first artificial intelligence model using first verification data; and training the second artificial intelligence model using second training data, wherein the second training data comprises the first verification data.

9. The medical auxiliary information generation method according to claim 8, further comprising:

verifying the trained second artificial intelligence model using second verification data, wherein the second verification data comprises at least part of the first training data.

10. The medical auxiliary information generation method according to claim 1, wherein the physiological image comprises an image captured through a camera into an esophagus of a patient.

11. A medical auxiliary information generation system, comprising:

a storage circuit, configured to store a physiological image; and a processor, coupled to the storage circuit, wherein the processor is configured to:

obtain the physiological image;

identify a target image region from the physiological image through at least one artificial intelligence model, wherein each pixel position in the target image region corresponds to an estimation value, and the estimation value meets a default condition;

determine at least one target pixel position in the target image region according to a numerical distribution of the estimation value; and generate medical auxiliary information according to the at least one target pixel position, wherein the medical auxiliary information carries prompt information related to the at least one target pixel position.

12. The medical auxiliary information generation system according to claim 11, wherein the operation of identifying the target image region from the physiological image through the at least one artificial intelligence model comprises:

inputting the physiological image to the at least one artificial intelligence model;

determining the estimation value corresponding to each pixel position in the physiological image according to an output of the at least one artificial intelligence model; and according to the estimation value corresponding to the each pixel position in the physiological image, determining the target image region in the physiological image.

13. The medical auxiliary information generation system according to claim 12, wherein the at least one artificial intelligence model comprises a first artificial intelligence model and a second artificial intelligence model, and the operation of determining the estimation value corresponding to the each pixel position in the physiological image according to the output of the at least one artificial intelligence model comprises:

according to an output of the first artificial intelligence model, obtaining a first estimation value corresponding to the each pixel position in the physiological image;

according to an output of the second artificial intelligence model, obtaining a second estimation value corresponding to the each pixel position in the physiological image; and determining the estimation value corresponding to the each pixel position in the physiological image according to the first estimation value and the second estimation value.

14. The medical auxiliary information generation system according to claim 12, wherein the operation of according to the estimation value corresponding to the each pixel position in the physiological image, determining the target image region in the physiological image comprises:

judging whether an estimation value corresponding to a first pixel position in the physiological image is greater than a default value; and in response to the estimation value corresponding to the first pixel position being greater than the default value, incorporating the first pixel position into the target image region.

15. The medical auxiliary information generation system according to claim 14, wherein the operation of determining the at least one target pixel position in the target image region according to the numerical distribution of the estimation value comprises:

comparing estimation values corresponding to a plurality of candidate pixel positions in the target image region; and determining the at least one target pixel position from the candidate pixel positions according to a comparison result.

16. The medical auxiliary information generation system according to claim 15, wherein the operation of determining the at least one target pixel position from the candidate pixel positions according to the comparison result comprises:

determining a candidate pixel position corresponding to a maximum estimation value among the candidate pixel positions as one of the at least one target pixel position.

17. The medical auxiliary information generation system according to claim 11, wherein the at least one target pixel position comprises a first target pixel position and a second target pixel position, and a distance between the first target pixel position and the second target pixel position is greater than a default distance value.

18. The medical auxiliary information generation system according to claim 11, wherein the at least one artificial intelligence model comprises a first artificial intelligence model and a second artificial intelligence model, and the processor is further configured to:

train the first artificial intelligence model using first training data;

verify the trained first artificial intelligence model using first verification data; and train the second artificial intelligence model using second training data, wherein the second training data comprises the first verification data.

19. The medical auxiliary information generation system according to claim 18, wherein the processor is further configured to:

verify the trained second artificial intelligence model using second verification data, wherein the second verification data comprises at least part of the first training data.

20. The medical auxiliary information generation system according to claim 11, further comprising:

a camera, coupled to the processor, wherein the physiological image comprises an image captured through the camera into an esophagus of a patient.

* * * * *